United States Patent
Keown et al.

(10) Patent No.: US 7,795,241 B2
(45) Date of Patent: Sep. 14, 2010

(54) DERIVATIVE PRODRUGS OF ETHINYL ESTRADIOL

(75) Inventors: James Keown, Kilkeel (GB); James William McIlroy, Belfast (GB); John Alexander King, Sallins (IE); Claire Gilligan, Belfast (GB); William Paul Armstrong, Belfast (GB)

(73) Assignee: Warner Chilcott Company, LLC, Fajardo, PR (US)

( * ) Notice: Subject to any disclaimer, the term of this patent is extended or adjusted under 35 U.S.C. 154(b) by 738 days.

(21) Appl. No.: 11/478,582

(22) Filed: Jul. 3, 2006

(65) Prior Publication Data

US 2007/0015740 A1 Jan. 18, 2007

Related U.S. Application Data

(60) Provisional application No. 60/698,865, filed on Jul. 12, 2005.

(51) Int. Cl.
*A61K 31/567* (2006.01)
*C07J 1/00* (2006.01)

(52) U.S. Cl. .................... 514/182; 552/625
(58) Field of Classification Search ........... 552/625; 514/182

See application file for complete search history.

(56) References Cited

U.S. PATENT DOCUMENTS

| | | | | |
|---|---|---|---|---|
| 2,205,627 | A * | 6/1940 | Scholz et al. | 552/625 |
| 2,840,508 | A | 6/1958 | Junkmann et al. | 167/74 |
| 3,766,223 | A | 10/1973 | Ercoli et al. | 552/509 |
| 3,828,081 | A | 8/1974 | Ercoli et al. | 260/397.2 |
| 3,916,002 | A | 10/1975 | Taubert et al. | 260/397.4 |
| 3,952,030 | A | 4/1976 | Chambers et al. | 260/397.4 |
| 3,989,828 | A * | 11/1976 | Aries | 514/171 |
| 4,002,747 | A | 1/1977 | van der Vies | 424/243 |
| 4,198,405 | A | 4/1980 | Enomoto et al. | 424/242 |
| 4,310,511 | A | 1/1982 | Holick | 424/59 |
| 4,774,236 | A * | 9/1988 | Cook et al. | 514/176 |
| 4,948,593 | A * | 8/1990 | Wright et al. | 424/473 |
| 5,116,828 | A * | 5/1992 | Miura et al. | 514/171 |
| 5,117,015 | A | 5/1992 | Yarino et al. | 552/541 |
| 5,610,149 | A | 3/1997 | Burrows et al. | 514/169 |
| 5,760,214 | A | 6/1998 | Zheng et al. | 540/109 |
| 5,888,996 | A | 3/1999 | Farb | 514/182 |
| 5,955,068 | A | 9/1999 | Gouin et al. | 424/78.17 |
| 5,989,581 | A | 11/1999 | Groenewegen | 424/433 |
| 6,028,207 | A | 2/2000 | Zheng et al. | 552/203 |
| 6,083,941 | A | 7/2000 | Farb | 514/177 |
| 6,375,930 | B2 | 4/2002 | Young et al. | 424/9.362 |
| 6,441,206 | B1 | 8/2002 | Mikkonen et al. | 552/540 |
| 2002/0131991 | A1 | 9/2002 | Milstein et al. | 424/439 |
| 2003/0077297 | A1 | 4/2003 | Chen et al. | 424/400 |
| 2005/0159399 | A1 | 7/2005 | King et al. | |
| 2005/0159609 | A1 | 7/2005 | King et al. | 552/509 |

FOREIGN PATENT DOCUMENTS

| | | |
|---|---|---|
| DE | 1 123 666 | 10/1959 |
| DE | 2 330 581 | 1/1975 |
| FR | 2 297 629 | 1/1975 |
| GB | 833582 | 4/1960 |
| JP | 35-004967 | 5/1960 |
| NL | 7 308 083 | 12/1974 |
| WO | WO 98/52965 | 11/1998 |
| WO | WO 03/082254 A1 | 10/2003 |

OTHER PUBLICATIONS

K. Parfitt, "Martindale—The Complete Drug Reference," 32ed, 1999, Pharmaceutical Press, pp. 1455-1458.

K. Fotherby, "Intrasubject Variability in the Pharmacokinetics of Ethynyloestradiol," Journal of Steroid Biochemistry and Molecular Biology, vol. 38, No. 6, 1991, pp. 733-736.

K. Fotherby, "Pharmacokinetics of Ethynyloestradiol in Humans," Methods and Findings in Experimental Clinical Pharmacology, 1982, 4(2), pp. 133-141.

E. Diczfalusy, O. Ferno, H. Fex, and B. Hogberg, "Long-Acting p-Alkoxyhydrocinnamic Acid Esters of Steroid Hormones," Acta Chemica Scandinavica, 1963, 17, pp. 2536-2547.

J. Fried and N.A. Abraham, "The Effect of Co-Solvents on Metal in Ammonia Reductions, The Formation of Dimeric Steroid Hormones," Tetrahedron Letters, 1964, No. 28, pp. 1879-1885.

H. Kuhl and H. Taubert, "A New Class of Long-Acting Hormonal Steroid Preparation: Synthesis of Oligomeric Estradiol Derivatives," Steroids, Jul. 1973, 22, pp. 73-87.

H. Kuhl and H. Taubert, "A New Class of Long-Acting Hormonal Steroid Preparation: Synthesis of Dimeric Ethynodiol and Nortestosterone, or Dimeric and Trimeric Androgens and of Some Dimeric Combinations of Steroids," Steroids, 1974, vol. 24, No. 5, pp. 613-626.

(Continued)

*Primary Examiner*—Barbara P Badio
(74) *Attorney, Agent, or Firm*—Fitzpatrick, Cella, Harper & Scinto

(57) ABSTRACT

The present invention is a prodrug derivative of ethinyl estradiol according to Formula I:

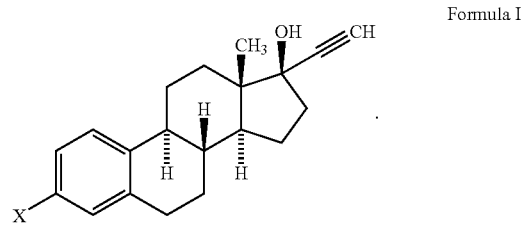

Formula I

4 Claims, No Drawings

OTHER PUBLICATIONS

H. Kuhl, W. Auerhammer, and H. Taubert, "Oligomeric Oestradiol Esters: A New Class of Long-Acting Oestrogens," Acta Endrocrinologica, 1976, 83, pp. 439-448.

R. Vitali, S. Gladiali, G. Falconi, G. Celasco, M.A. Saccani, and R. Gardi, "Disteroidyl Ethers. 1. Synthesis and Oral Long-Lasting Uterotrophic Activity of 1,3,5(10)-Estratrien-17-yl Enol Ethers of 3-Keto Steroids," Journal of Medicinal Chemistry, 1977, vol. 20, No. 3, pp. 359-364.

A. Ius, G. Meroni, and L. Ferrara, "Two Dimers, 4:4'- and 2:2'-Di[estradiol], Obtained by Chemical Oxidative Coupling of Estradiol," Journal of Steroid Biochemistry, 1977, vol. 8, pp. 1259-1261.

D. Rabouin, V. Perron, B. N'Zemba, R. Gaudreault, and G. Berube, "A Facile Synthesis of ç Symmetric 17β-Estradiol Dimers," Bioorganic & Medicinal Chemistry Letters, 2003, 13, pp. 557-560.

Hu Zheng et al., Abstract of "Studies on polymer-supported drugs: synthesis of poly(ethylene glycol)-estrogen compounds," Chemical Abstracts Service (XP002322263), and Yaoxue Xuebao (Database Accession No. 1988:423178), 1987, 22(8), 637-40.

Huai-De Shu et al., Abstract of "Structure-activity relationships of estradiol derivatives," Chemical Abstracts Service (XP002322264), and Yaoxue Xuebao (Database Accession No. 1979:604845), 1979, 14(6), 343-8.

W. Dirscherl, "Uber Kohlensaurederivate des Follikelhormons. 7. Mitteilung uber Sexualhormone und verwandte Stoffe" Hoppe Seyler Zeitschrift Fur Physiol. Chemie, vol. 239, 1936, pp. 49-52. Translation included.

Thallapally, P. K. et al., "Polymorphism of 1,3,5-Trinitrobenzene Induced by a Trisindane Additive," Angewandte Chemie, pp. 1149-1155, vol. 43 (2004).

Guguta, C. et al., "Structural Diversity of Ethinyl Estradiol Solvates," Crystal Growth & Design, vol. 8, No. 3, pp. 823-831 (2008).

FDA, "Guidance for Industry; ANDAs: Pharmaceutical Solid Polymorphism—Chemistry, Manufacturing, and Controls Information," pp. 1-10 (Jul. 2007).

Ishida, T. et al., "Physicochemical Properties of Crystalline Forms of Ethynylestradiol Solvates: Comparison of Thermal Behavior with X-ray Crystal Structure," Journal of Pharmaceutical Sciences, vol. 78, No. 4, pp. 274-280.

Ebian, A. R. et al., "Polymorphism and Solvation of Ethinyl Oestradiol," Pharm. Acta Helv., vol. 54, No. 4, pp. 111-114 (1979).

Lee et al., "Crystal Properties (Polymorphism)," Preformulation in Solid Dosage Form Development, vol. 178, pp. 580-583 (M. C. Adeyeye & H. G. Brittain Eds.).

"Polymorphism" and "Water: A Major Environmental Variable," Remington—The Science and Practice of Pharmacy, 20th Edition, Chapters 13 and 38, pp. 181-182 and 702, 710.

Yokogawa, K. et al., "Selective Delivery of Estradiol to Bone by Aspartic Acid Oligopeptide and it Effects on Ovariectomized Mice," Endocrinology, vol. 142(3), pp. 1228-1233 (2001).

Park, J-S. et al., "Use of CP/MAS solid-state NMR for the characterization of solvate molecules within estradiol crystal forms," European J. Pharmaceutics & Biopharmaceutics, vol. 60, pp. 407-412 (2005).

Philip L. Lorenzi et al., "Amino Acid Ester Prodrugs of 2-Bromo-5,6-dichloro-1-(β-D-ribofuranosyl) benzimidazole Enhance Metabolic Stability in Vitro and in Vivo," Journal of Pharmacology and Experimental Therapeutics, May 18, 2005; 314(2): 883-890.

Young S. Rho et al., "Synthesis of New Anthracycline Derivatives Containing Pyruvic, Aspartic, or N-Acetylaspartic Acid Molecule," Synthetic Communications, 2002; 32(13): 1961-1975.

Christopher P. Landowski et al., "Targeted delivery to PEPT1-overexpressing cells: Acidic, basic, and secondary floxuridine amino acid ester prodrugs," Molecular Cancer Therapeutics, Apr. 2005; 4(4): 659-667.

G.L. Amidon et al., "Improving Intestinal Absorption of Water-Insoluble Compounds: A Membrane Metabolism Strategy," Journal of Pharmaceutical Sciences, Dec. 1980; 69(12): 1363-1368.

Allan P. Gray et al., "Steroid Antifertility Agents. Ionic Complexes of Basic Derivatives for Prolonged Action,"Journal of Medicinal Chemistry, Jul. 1978; 21(7): 712-715.

* cited by examiner

DERIVATIVE PRODRUGS OF ETHINYL ESTRADIOL

CROSS REFERENCE TO RELATED APPLICATIONS

This application claims the benefit of U.S. Provisional Application Ser. No. 60/698,865 filed on Jul. 12, 2005.

BACKGROUND OF THE INVENTION

Field of the Invention

Unbound 17β-estradiol is the most active, naturally occurring human estrogen. However, due to poor absorption and extensive first-pass metabolism in the gastrointestinal tract and liver following oral absorption, it is not generally orally active. Methods of increasing activity have included the use of micronized drugs to improve absorption and the use of prodrugs such as estradiol-17-valerate and equine estrogens which are a combination of sulfate and glucuronide derivatives.

Another method of increasing activity is to alter the structure of the 17β-estradiol. Ethinyl estradiol is an example of this. The ethinyl group on the 17 position greatly reduces liver first-pass metabolism compared to 17β-estradiol, enabling the compound to be more active than the natural estrogen, 17β-estradiol.

Ethinyl estradiol is the most common estrogen used in contraceptive preparations. Given its increased potency over 17β-estradiol it is used in comparatively lower doses (i.e., orally 15 to 50 µg per day). It is also more potent by other routes of administration, i.e., vaginally where it can be employed at a daily dose of 15 µg (see U.S. Pat. No. 5,989,581). It has also been used in Hormone Replacement Therapy although to a lesser extent than 17β-estradiol.

While ethinyl estradiol has been preferred over 17β-estradiol, there are some disadvantages associated with the use of ethinyl estradiol. For example, not all of the ethinyl estradiol that is administered is biologically available. Ethinyl estradiol is metabolized in the intestinal wall and liver, which affects its bioavailability. Moreover, its bioavailability may vary somewhat from individual to individual. In addition, it has been observed that as ethinyl estradiol is metabolized in the liver, enterohepatic recycling occurs.

A novel prodrug of ethinyl estradiol, that improves bioavailability would be highly advantageous.

SUMMARY OF THE INVENTION

The present invention is a prodrug derivative of ethinyl estradiol according to Formula I:

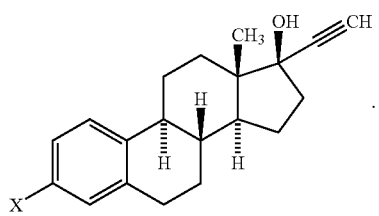

Formula I and enantiomers and pharmaceutically acceptable salts thereof; wherein X is selected from the group consisting of

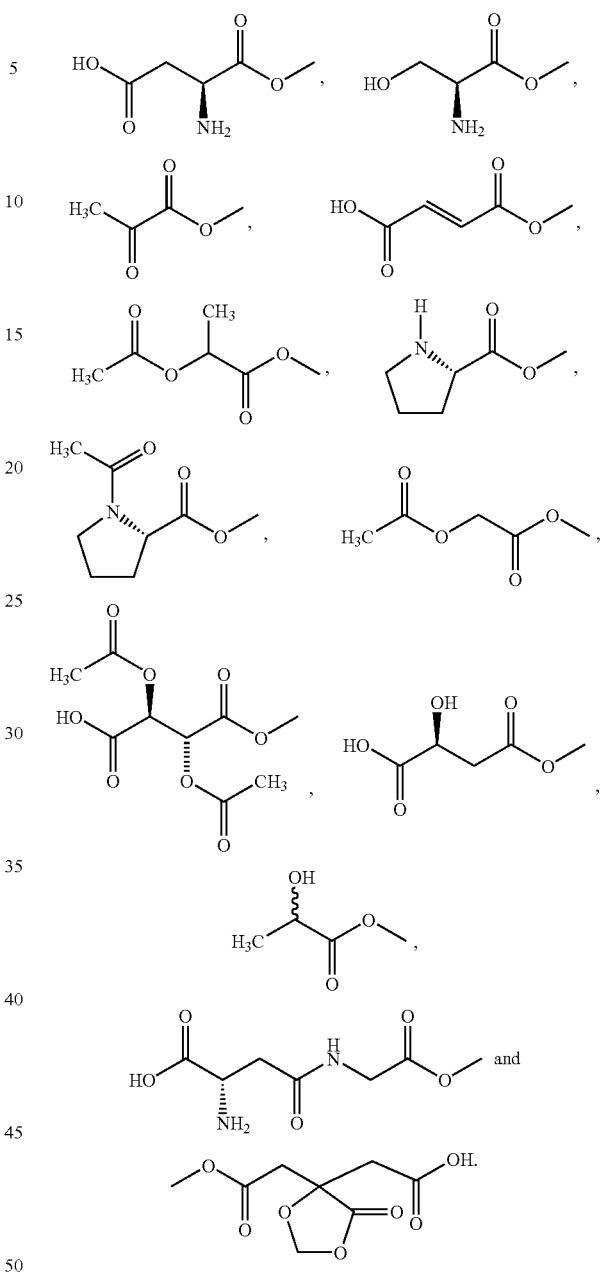

The present invention includes a pharmaceutical dosage unit comprising (a) a prodrug derivative of ethinyl estradiol according to Formula I, and (b) one or more pharmaceutically acceptable excipients.

In another aspect of the present invention, a method of providing contraception is provided. The method comprises the step of administering to a patient in need thereof, an effective amount of a prodrug derivative of ethinyl estradiol of the invention, for an effective period of time.

In yet another aspect of the invention, a method of providing hormone treatment therapy is provided. The method comprises the step of administering to a patient in need thereof, an effective amount of a prodrug derivative of ethinyl estradiol of the invention, for an effective period of time.

DETAILED DESCRIPTION OF THE INVENTION

For the purposes of the present invention a prodrug is an entity, which either comprises an inactive form of an active drug or includes a chemical group which confers preferred characteristics on the drug.

For the purposes of the present invention, room temperature is understood to mean 25° C.+/−5° C.

In the present invention, the prodrug derivative of ethinyl estradiol has the structural formula:

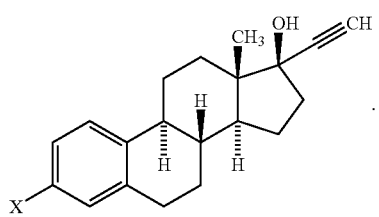

Formula I wherein X is selected from the group consisting of

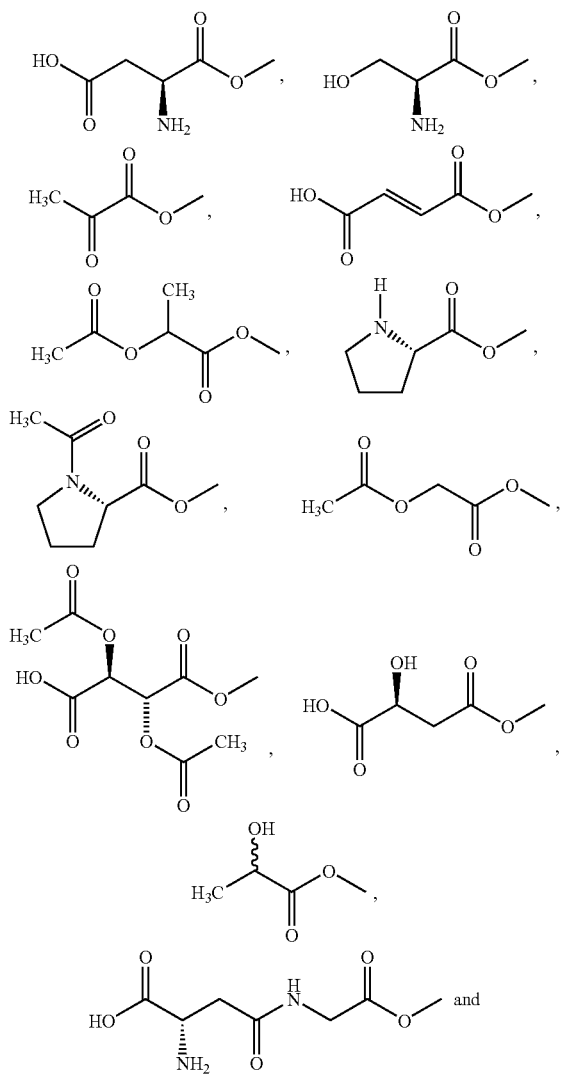

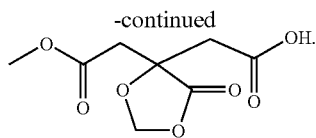

In a preferred embodiment, X is

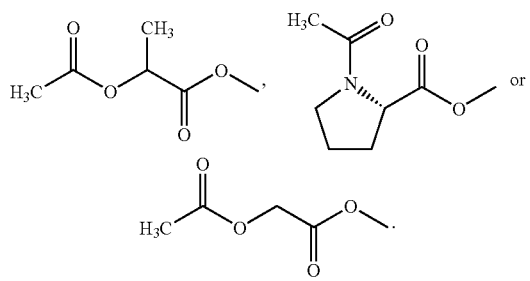

Notably, X attaches to the ethinyl estradiol compound at the 3'C position of the ethinyl estradiol compound. It should be understood that the inventive compounds of Formula I include all their enantiomers and their pharmaceutically acceptable salts.

As used herein, the phrase "pharmaceutically acceptable salt" refers to a salt that retains the biological effectiveness of the free acids and bases of a specified compound and that is not biologically or otherwise undesirable.

The prodrug derivative of ethinyl estradiol of the present invention may be combined with one or more pharmaceutically acceptable excipients to form a pharmaceutical dosage unit.

Excipients useful herein include a wide variety of additives, or ingredients, such as, fillers, diluents (solid and liquid), biocompatible polymers (such as organopolysiloxanes, polyurethanes and polymethylacrylates), skin penetrators and penetration enhancers, solubilizers, lubricants, stabilizers, flow control agents, colorants, glidants, effervescent agents, sweeteners, flavors, perfumes, and the like.

Other steroids, e.g., progestogens may be included in the pharmaceutical dosage unit. Exemplary progestogens include norethindrone, drospirenone, trimegestone, levonorgestrel, desogestrel, 3-ketodesogestrel, gestodene, demegestone, dydrogesterone, medrogestone, medroxy progesterone and esters thereof and the like.

The pharmaceutical dosage unit may be in an orally ingestible form, such as tablets, capsules, chewable tablets or capsules, troches, liquid suspensions, pills, or sustained release dosage forms. Alternatively, the pharmaceutical dosage unit may be a transdermal delivery system. Or in another embodiment the pharmaceutical dosage unit may be a topical composition such as a gel, cream, ointment, liquid and the like. Or in an alternative embodiment, the pharmaceutical dosage unit may be designed for vaginal administration e.g., a vaginal ring. The steroidal prodrugs of ethinyl estradiol may be synthesized using the methods described herein. These methods may be modified or alternative synthesis methods may be employed as desired. The synthesis methods typically begin with ethinyl estradiol as the starting material, but could also begin with estrone. It should be understood, however, that where ethinyl estradiol is indicated, derivatives of ethinyl estradiol may be used.

In one embodiment, a fumaric acid ethinyl estradiol ester may be formed in accordance to Reaction Sequence 1. The reaction combines ethinyl estradiol and maleic anhydride in the presence of a base catalyst, e.g., sodium hexamethyldisilylamide (NaHMDS) and a solvent, e.g., tetrahydrofuran (THF) at −78° C. Deprotecting agents such as hydrochloric acid (HCl) and ether are then added to yield the desired product.

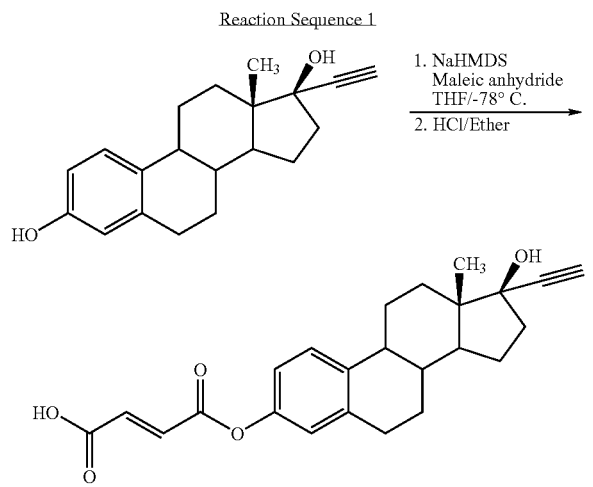

Reaction Sequence 2 provides a route to synthesize a derivative ethinyl estradiol ester compound by reacting ethinyl estradiol or a derivative thereof with a compound having the structure

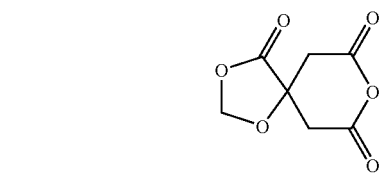

in the presence of NaHMDS, maleic anhydride, and THF (−78° C.) to form an intermediate compound, which is then reacted with HCl/dioxane.

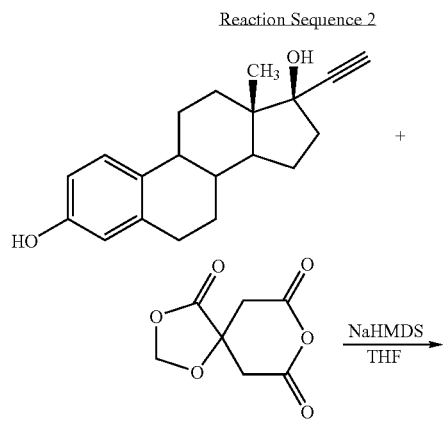

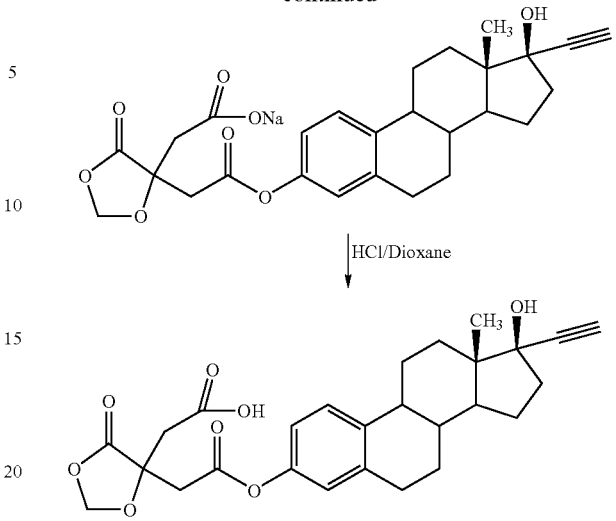

In another embodiment, a prodrug compound of the invention may be synthesized by reacting ethinyl estradiol directly with a compound having a structure

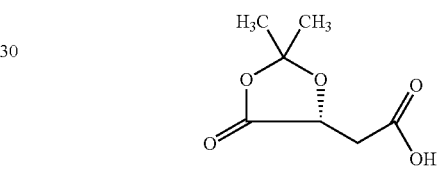

The intermediate compound undergoes deprotection and forms a malic acid ethinyl estradiol ester, as depicted in Reaction Sequence 3.

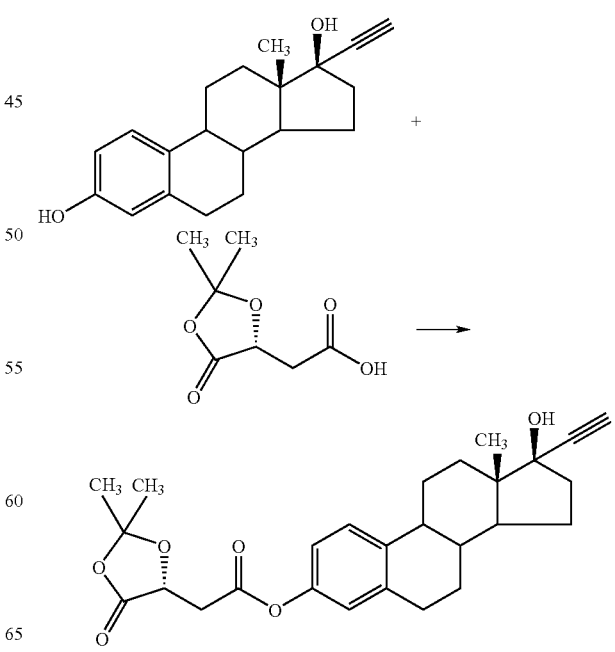

Followed by deprotection step

Reaction Sequence 3

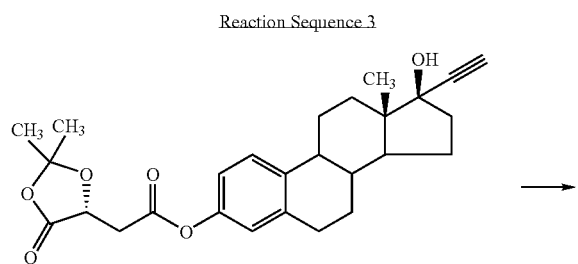

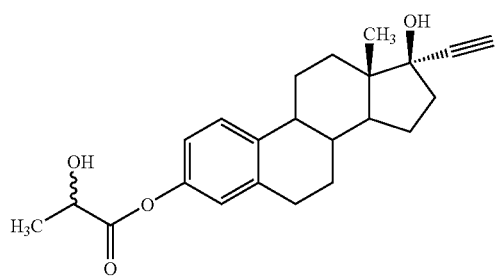

In Reaction Sequence 5, an acetoxyacetic acid ester of ethinyl estradiol is synthesized by reacting ethinyl estradiol with acetoxyacetic acid.

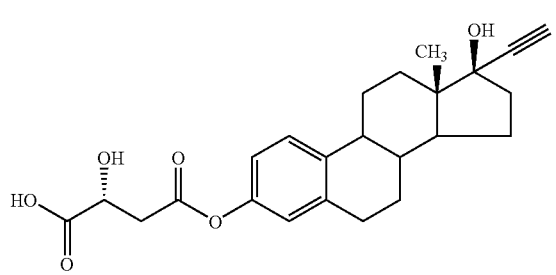

In Reaction Sequence 4, ethinyl estradiol is reacted with pyruvic acid. An intermediate compound is formed, which is then treated with a deprotecting agent, such as sodium borohydride ($NaBH_4$). The resulting compound is the lactic acid ethinyl estradiol ester.

Reaction Sequence 5

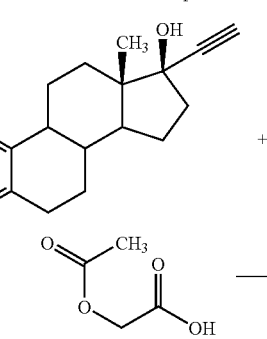

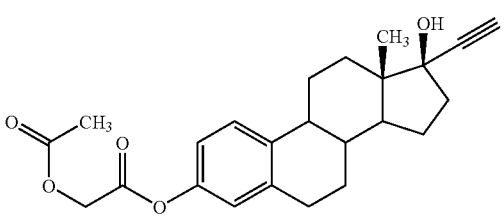

A prolinate ethinyl estradiol ester derivative may be formed in accordance to Reaction Sequence 6. Ethinyl estradiol is combined with Boc-proline in the presence of a coupling agent, e.g., DCC, forming an intermediate compound. A deprotecting agent, such as HCl/dioxane, is then added to form the desired prolinate ethinyl estradiol ester derivative.

Reaction Sequence 4

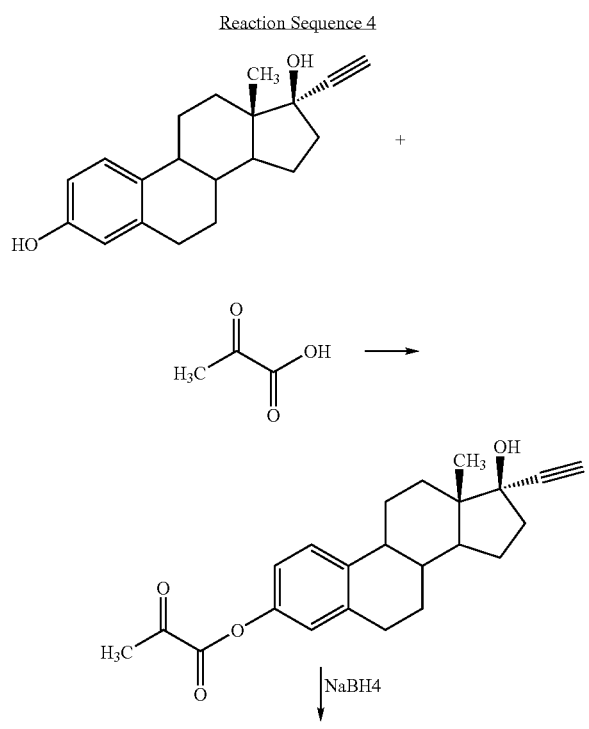

Reaction Sequence 6

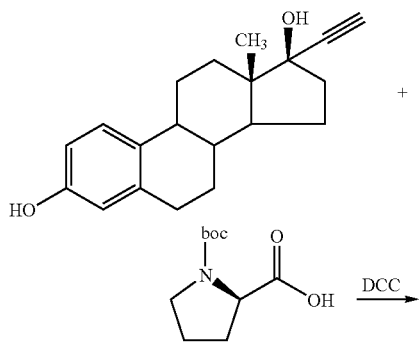

-continued

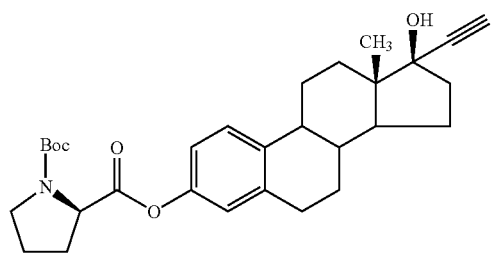

↓ HCl/Dioxane

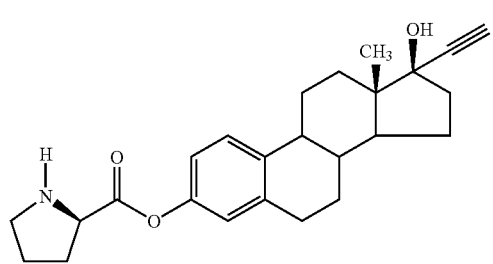

Reaction Sequence 7 provides a synthesis route for making a serine ethinyl estradiol ester derivative. Ethinyl estradiol is combined with Boc-serine. An intermediate compound is formed which is then reacted in the presence of a deprotecting agent, such as HCl/dioxane, to produce the serine ethinyl estradiol ester.

Reaction Sequence 7

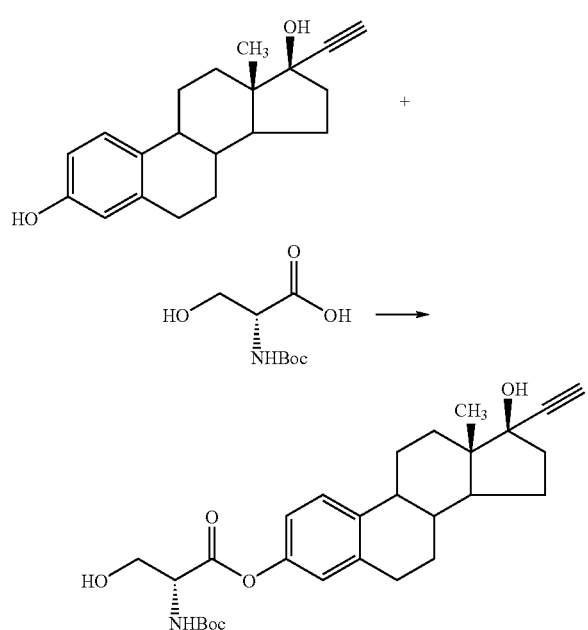

↓ HCl/Dioxane

-continued

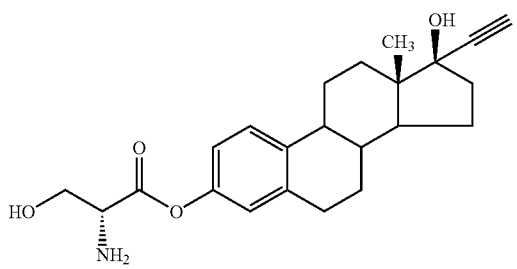

HCl

Reaction Sequence 8 provides a synthesis route for making the acetyl lactic acid ester derivative of ethinyl estradiol. Ethinyl estradiol is combined with acetyl lactic acid to form the desired compound.

Reaction Sequence 8

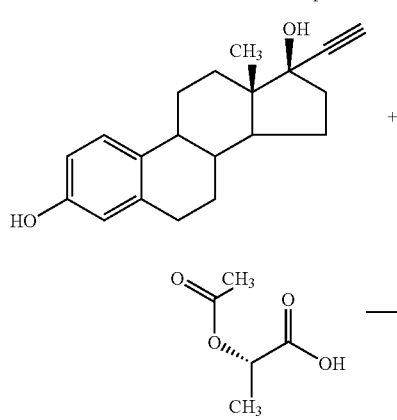

Utilizing Reaction Sequence 9, ethinyl estradiol is combined with a compound having the structure

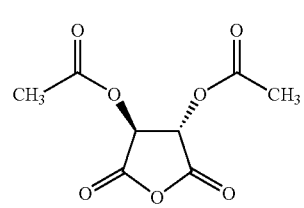

to form an intermediate compound that is then treated with a deprotecting agent, such as HCl/ether, to yield diacetyltartaric acid ethinyl estradiol ester.

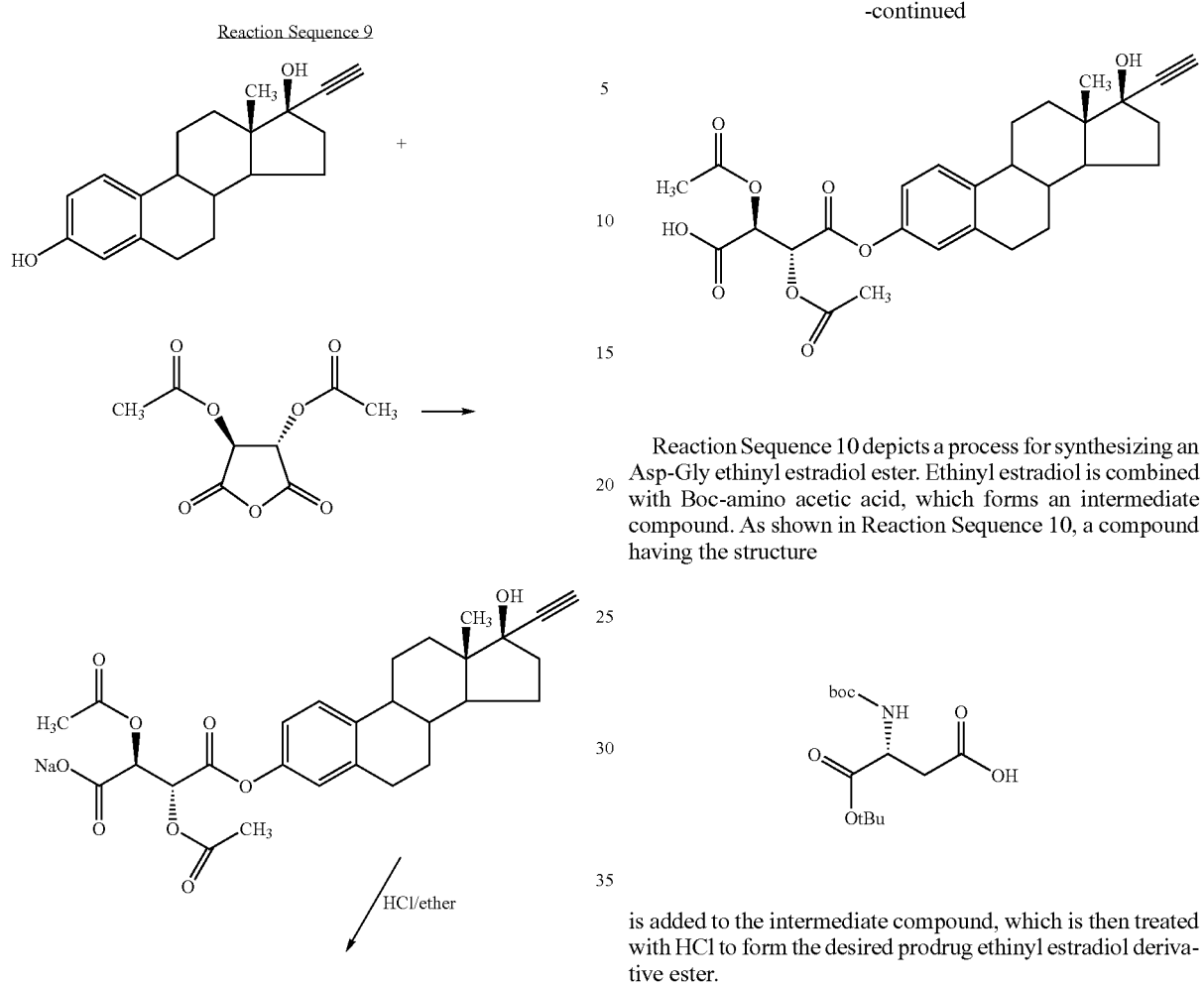

Reaction Sequence 10 depicts a process for synthesizing an Asp-Gly ethinyl estradiol ester. Ethinyl estradiol is combined with Boc-amino acetic acid, which forms an intermediate compound. As shown in Reaction Sequence 10, a compound having the structure is added to the intermediate compound, which is then treated with HCl to form the desired prodrug ethinyl estradiol derivative ester.

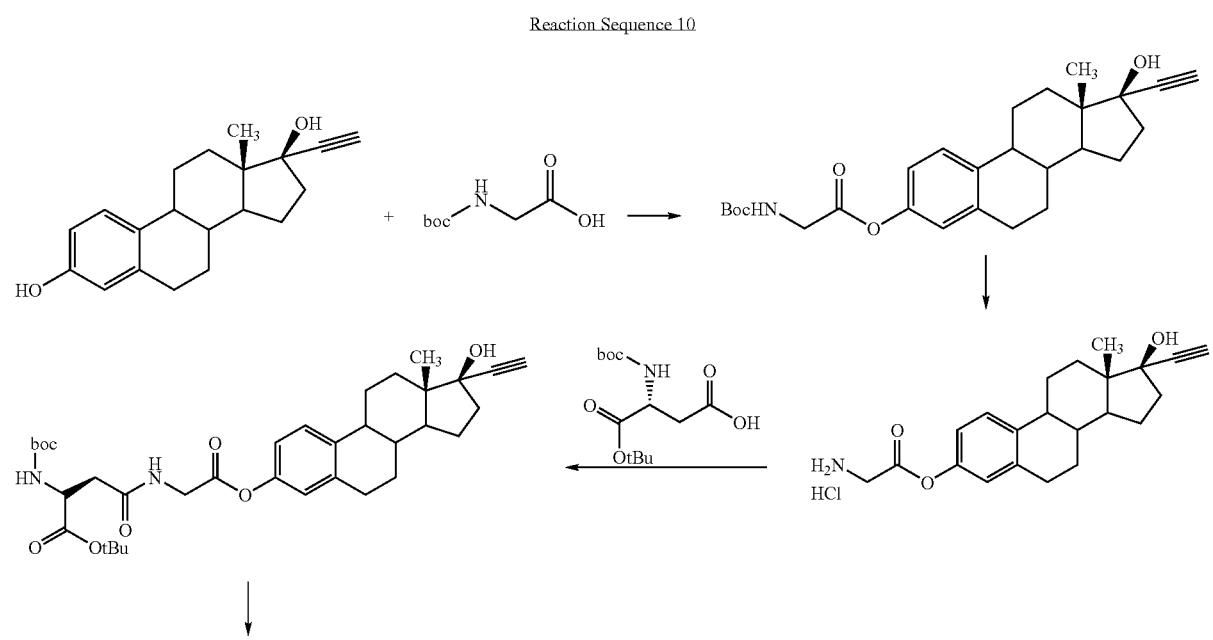

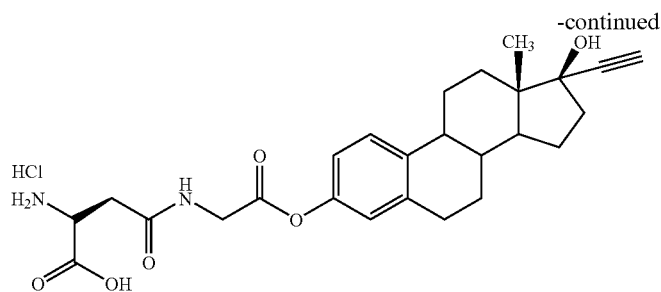

Reaction Sequence 11 starts by combining ethinyl estradiol with Boc-aspartic acid t-butyl $C_4$. This combination forms an intermediate compound, which is then treated with a deprotecting agent, such as HCl/dioxane to yield the aspartic acid ethinyl estradiol ester.

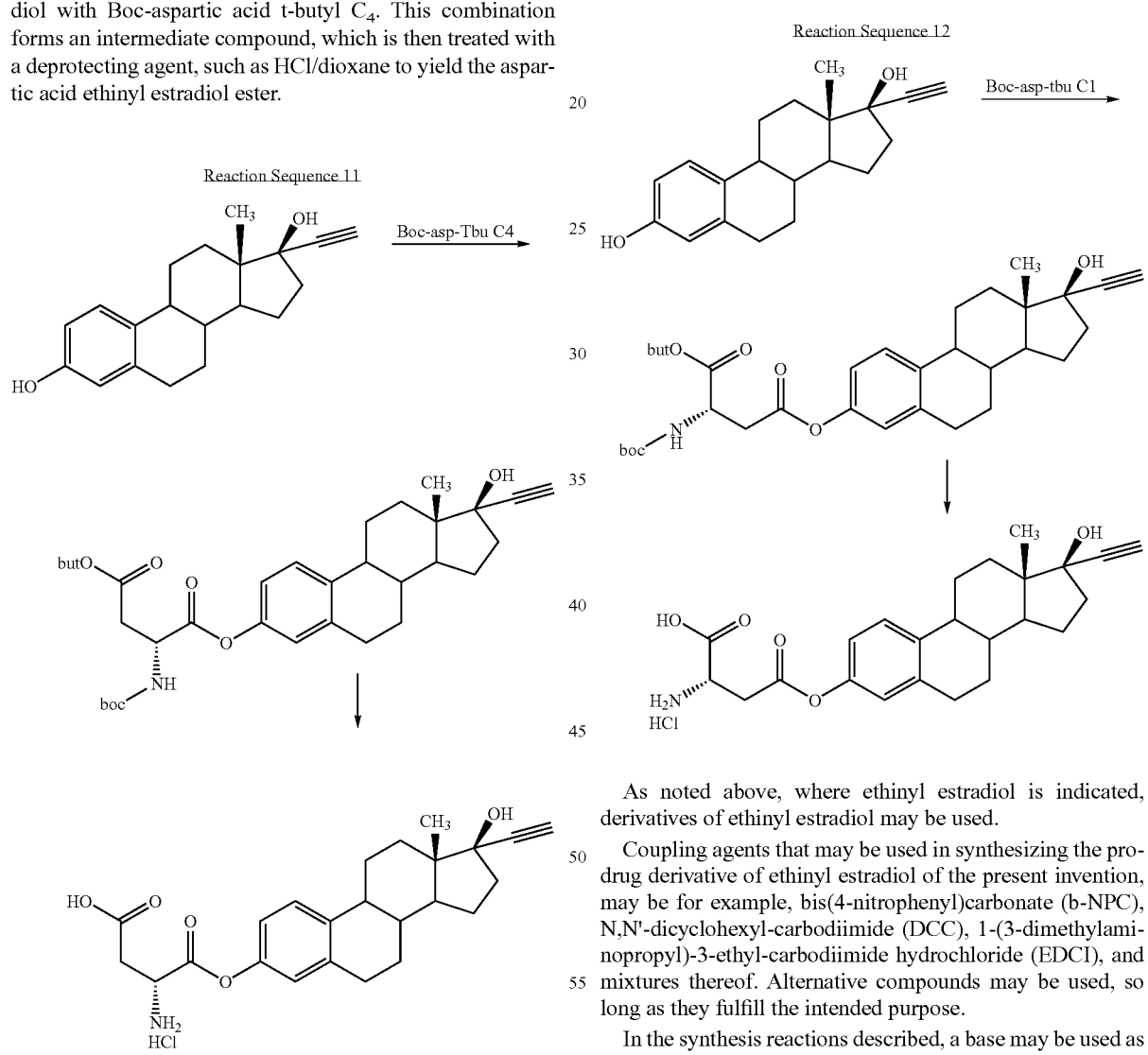

Utilizing Reaction Sequence 12, ethinyl estradiol is reacted with Boc-aspartic acid t-butyl $C_1$, which forms an intermediate compound. A deprotecting agent, such as HCl/dioxane is combined with the intermediate compound to form the desired aspartic acid ethinyl estradiol ester.

As noted above, where ethinyl estradiol is indicated, derivatives of ethinyl estradiol may be used.

Coupling agents that may be used in synthesizing the prodrug derivative of ethinyl estradiol of the present invention, may be for example, bis(4-nitrophenyl)carbonate (b-NPC), N,N'-dicyclohexyl-carbodiimide (DCC), 1-(3-dimethylaminopropyl)-3-ethyl-carbodiimide hydrochloride (EDCI), and mixtures thereof. Alternative compounds may be used, so long as they fulfill the intended purpose.

In the synthesis reactions described, a base may be used as a catalyst. Suitable bases include, but are not limited to 4-dimethylamino pyridine (DMAP), triethylamine, NaHMDS or mixtures thereof.

Deprotecting agents may be used in the synthesis reactions when needed. Non-limiting examples include HCl, dioxane, ether, sodium borohydride ($NaBH_4$), and mixtures thereof such as, for example, acetic acid:THF:water.

Solvents that may be used in the synthesis reactions are for example, tetrahydrofuran (THF), methanol, pyridine, chloroform, dichloromethane (DCM), and the like. However, it should be noted that many other organic solvents may be suitable.

To increase the purity of the prodrug derivative of ethinyl estradiol, the prodrug may be treated to one or more washing steps, one or more drying steps, and/or a recrystallization step.

The washing step may be used to rinse the precipitate that is formed by the prodrug derivative of ethinyl estradiol. As noted, one or more washing steps may be used. Water, sodium hydroxide, or any suitable alternative can be generally used for washing purposes.

As previously noted, the purity may be increased by subjecting the prodrug derivative of ethinyl estradiol to one or more drying steps. The drying step may be performed by various methods, including but not limited to, air drying, vacuum drying, oven drying, filtration, and the like. Drying may be enhanced by using a drying agent such as magnesium sulfate to assist in drying the product.

The prodrug derivative of ethinyl estradiol of the present invention may be used for providing contraception. A therapeutically effective amount of the prodrug derivative of ethinyl estradiol of the invention, is administered to a patient in need thereof, for an effective period of time. Preferably, the prodrug is administered in combination with a progestogen.

The prodrug derivative of ethinyl estradiol of the invention can also be used in providing hormone treatment therapy. Such a method of treatment would comprise the step of administering to a patient in need thereof, a therapeutically effective amount of a prodrug derivative of ethinyl estradiol of the invention, for an effective period of time.

The prodrugs of ethinyl estradiol of the present invention are administered in a "therapeutically effective amount." This is understood to mean a sufficient amount of a compound or dosage unit that will positively modify the symptoms and/or condition to be treated. The therapeutically effective amount can be readily determined by those of ordinary skill in the art, but of course will depend upon several factors. For example, one should consider the condition and severity of the condition being treated, the age, body weight, general health, diet, and physical condition of the patient being treated, the duration of the treatment, the nature of concurrent therapy, the particular active ingredient being employed, the particular pharmaceutically-acceptable excipients utilized, the time of administration, method of administration, rate of excretion, drug combination, and any other relevant factors.

The prodrugs of the invention are preferably administered orally, transdermally, topically or vaginally. The preferred dosage forms are tablets, gels, creams or vaginal rings.

The prodrug derivative of ethinyl estradiol compounds of the present invention have been characterized using various analytical methods. For example, high performance liquid chromatography (HPLC) was used to establish the purity of the synthesized product. $^1$H and $^{13}$C nuclear magnetic resonance (NMR), mass spectrometry and infrared (IR) spectroscopy were used to verify its structure. Moreover, the product was further characterized by determining its melting point.

Specific embodiments of the invention will now be demonstrated by reference to the following examples. It should be understood that these examples are disclosed solely by way of illustrating the invention and should not be taken in any way to limit the scope of the present invention.

Example 1

Example 1 provides stability, solubility and rate of hydrolysis measurements for ethinyl estradiol acetoxy acetate. Solubility was performed in water. All stability was conducted at 40° C./75% RH, with the prodrug being assayed at specific time-points for degradation to the parent compound, ethinyl estradiol. The time-points for stability were T=0 months, T=2 weeks, T=1 month, T=3 months and T=6 months.

Hydrolysis studies refer to the rate of hydrolysis to the parent drug, ethinyl estradiol. Hydrolysis was conducted in the following manner:

(1) 1 mL of a solution containing the prodrug, 2.8 mL of water and 0.1 mL of 0.5N NaOH were combined;

(2) the resulting solution was vortexed for 10 seconds;

(3) the mixture was then left to stand for specific time intervals (e.g., 5 minutes, 15 minutes, etc.);

(4) the mixture was then neutralized with 0.1 mL of a buffer; and (5) the solutions were finally injected to quantify the disappearance of the prodrug and the formation of the parent compound.

The results of these studies on ethinyl estradiol acetoxy acetate, which may be prepared in accordance with reaction sequence 5, are shown in TABLE 1.

TABLE 1

| Prodrug | Investigation | | Assay | | |
| --- | --- | --- | --- | --- | --- |
| Monomer | Solubility | Hydrolysis | T = 0 | T = 2 W | T = 1 M |
| Ethinyl Estradiol Acetoxy Acetate | 2.0 ug/mL | 100% (5 min) | 97.8 | 97.2 | 97.0 |

The following outlines the conditions utilized for analysis of this prodrug. Analysis was conducted using High-Performance Liquid Chromatography (HPLC). The retention time for ethinyl estradiol acetoxy acetate was approximately 15.0 minutes using these conditions.

| | |
| --- | --- |
| Column: | Zorbex SB-C18 5 μm, 4.6 × 250 mm |
| Flow rate: | 1.0 mL/min |
| Temperature: | Ambient |
| Wavelength: | 210 nm |
| Injection Volume | 10 μL |
| Sample solvent: | MeCN (acetonitrile) |
| Retention Time: | ~15.0 minutes |

As can be seen in TABLE 1 above, ethinyl estradiol acetoxy acetate has a solubility of 2.0 ug/ml in water, and 100% of this compound hydrolyzes to ethinyl estradiol in 5 minutes (by the method described above). After 1 month at 40° C./75% RH, 97% of the compound still exists as ethinyl estradiol acetoxy acetate.

Example 2

The results of solubility, rate of hydrolysis and stability for ethinyl estradiol lactate-acetate, which may be prepared in accordance with reaction sequence 8, are shown in TABLE 2.

TABLE 2

| Prodrug Monomer | Investigation | | Assay (%) | | | |
|---|---|---|---|---|---|---|
| | Solubility | Hydrolysis[3] | T = 0 | T = 1 M | T = 3 M | T = 6 M |
| Ethinyl Estradiol Lactate-Acetate | 2.4 ug/mL | 100% (5 min) | 94.43 | 93.67 | 95.91 | 95.89 |

The following outlines the conditions utilized for analysis of this prodrug. Analysis was conducted using HPLC. The retention time for ethinyl estradiol lactate acetate was approximately 11.0 minutes using these conditions.

| Column: | Symmetry Shield RP$_{18}$ 5 μm, 4.6 × 250 mm |
| Flow rate: | 1.0 mL/min |
| Temperature: | Ambient |
| Wavelength: | 210 nm |
| Injection Volume | 10 μL |
| Sample solvent: | MeCN (acetonitrile) |
| Retention Time: | ~11.0 minutes |

As can be seen from TABLE 2, the solubility of ethinyl estradiol lactate acetate was 2.4 ug/ml. From the hydrolysis studies, 100% of this compound hydrolyzes to ethinyl estradiol in 5 minutes (by the method described above). After 6 months at 40° C./75% RH, 95.9% of the compound still exists as the prodrug.

Example 3

The results of stability for ethinyl estradiol N-acetyl proline, which may be prepared in accordance with reaction sequence 6, are shown in TABLE 3.

TABLE 3

| | Assay(%) | |
|---|---|---|
| Prodrug Monomer | T = 0 | T = 2 W |
| Ethinyl Estradiol N-Acetyl Prolinate | 97.2 | 96.6 |

The following outlines the conditions utilized for analysis of the prodrug. Analysis was conducted using HPLC. The retention time for ethinyl estradiol N-acetyl proline was approximately 15.0 minutes using these conditions.

| Column: | Luna C18, 5.0 μm, 250 mm × 4.6 mm |
| Flow rate: | 1.0 mL/min |
| Temperature: | Ambient |
| Wavelength: | 210 nm |
| Injection Volume | 10 μL |
| Sample solvent: | MeCN:H$_2$O (50:50) |
| Retention Time: | ~15.5 minutes |
| Mobile phase: | MeCN/0.1M Formic acid (50:50) |

As can be seen from TABLE 3, after 2 weeks at 40° C./75% RH, 96.6% of the compound still exists as the prodrug.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A compound having the following formula:

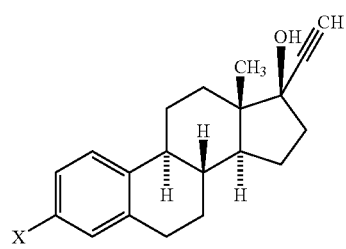

and enantiomers and pharmaceutically acceptable salts thereof, wherein X is

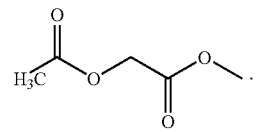

2. A pharmaceutical dosage unit comprising:
(a) a compound having the following formula:

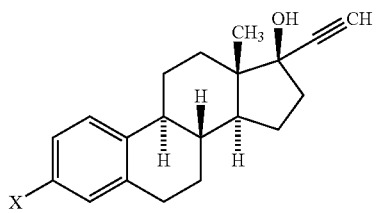

and enantiomers and pharmaceutically acceptable salts thereof, wherein X is

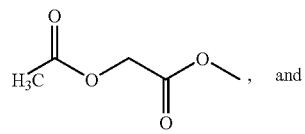

, and b) one or more pharmaceutically acceptable excipients.

3. A method of providing contraception comprising the step of:
   administering to a patient in need thereof, an effective amount of said compound of claim 1, for an effective period of time.

4. A method of providing hormone treatment therapy to a patient in need thereof, comprising the step of:
   administering to said patient in need thereof, an effective amount of said compound of claim 1, for an effective period of time.

* * * * *